United States Patent
Burbidge et al.

(10) Patent No.: US 10,596,108 B2
(45) Date of Patent: *Mar. 24, 2020

(54) METHOD FOR TREATING A SWALLOWING DISORDER

(71) Applicant: NESTEC S.A., Vevey (CH)

(72) Inventors: Adam Burbidge, Arzier (CH); Jan Engmann, Lausanne (CH); Kala Marie Kaspar, Lausanne (CH); Michael Jedwab, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 527 days.

This patent is subject to a terminal disclaimer.

(21) Appl. No.: 14/891,403

(22) PCT Filed: May 16, 2014

(86) PCT No.: PCT/EP2014/060038
§ 371 (c)(1),
(2) Date: Nov. 16, 2015

(87) PCT Pub. No.: WO2014/184329
PCT Pub. Date: Nov. 20, 2014

(65) Prior Publication Data
US 2016/0081923 A1     Mar. 24, 2016

(30) Foreign Application Priority Data

May 17, 2013 (EP) .................................. 13168363

(51) Int. Cl.
| A61K 9/00 | (2006.01) |
| A23L 2/52 | (2006.01) |
| A61K 47/36 | (2006.01) |
| A61K 9/10 | (2006.01) |
| A23L 29/206 | (2016.01) |
| A23L 33/10 | (2016.01) |
| A23L 33/00 | (2016.01) |
| A61K 47/46 | (2006.01) |

(52) U.S. Cl.
CPC .............. *A61K 9/0053* (2013.01); *A23L 2/52* (2013.01); *A23L 29/206* (2016.08); *A23L 33/10* (2016.08); *A23L 33/40* (2016.08); *A61K 9/0095* (2013.01); *A61K 9/10* (2013.01); *A61K 47/36* (2013.01); *A61K 47/46* (2013.01); *A23V 2002/00* (2013.01)

(58) Field of Classification Search
CPC .......... A23L 2/52; A23L 29/206; A23L 33/40; A23L 33/10; A61K 9/0095; A61K 47/36; A61K 9/101; A61K 9/0053; A61K 47/46; A23V 2002/00

See application file for complete search history.

(56) References Cited

U.S. PATENT DOCUMENTS

2014/0004045 A1* 1/2014 Mendenhall ......... A61K 9/0056
424/9.1
2014/0294787 A1* 10/2014 Burbidge ........... A61K 31/7048
424/93.41

FOREIGN PATENT DOCUMENTS

| JP | 2005187362 | 7/2005 |
| JP | 2009256216 | 11/2009 |
| JP | 2012188383 | 10/2012 |
| WO | 03011051 | 2/2003 |
| WO | 2004069179 | 8/2004 |
| WO | 2006054886 | 5/2006 |
| WO | 2010050541 | 5/2010 |
| WO | 2010122332 | 10/2010 |
| WO | 2012117065 | 9/2012 |

OTHER PUBLICATIONS https://www.engineersedge.com/physics/water_density_viscosity_specific_weight_13146.htm (accessed Nov. 12, 2018).*
Ishihara et al. "Swallowing profiles of food polysaccharide gels in relation to bolus rheology" Food Hydrocolloids, vol. 25, pp. 1016-1024.

* cited by examiner

*Primary Examiner* — Robert S Cabral
(74) *Attorney, Agent, or Firm* — K&L Gates LLP

(57) ABSTRACT

This invention relates to a method for treating a swallowing disorder in a patient suffering from aspiration before, during and/or after the swallowing reflex, and to a bolus for use in the treatment of a swallowing disorder in such a patient.

7 Claims, No Drawings

METHOD FOR TREATING A SWALLOWING DISORDER

CROSS REFERENCE TO RELATED APPLICATIONS

The present application is a National Stage of International Application No. PCT/EP2014/060038, filed on May 16, 2014, which claims priority to European Patent Application No. 13168363.3, filed on May 17, 2013, the entire contents of which are being incorporated herein by reference.

FIELD OF THE INVENTION

This invention relates to a method for treating a swallowing disorder in a patient suffering from aspiration and to a bolus for use in the treatment of a swallowing disorder in such a patient.

BACKGROUND OF THE INVENTION

Dysphagia is the medical term for the symptom of difficulty in swallowing. Current evidence suggests that 22% of adults over the age of 50 years, and most adults by age 80 years, experience swallowing difficulty. Oral nutrition is the desirable goal for every dysphagic patient, but in some cases may not be possible or appropriate. If adequate nutrition cannot be achieved, or if aspiration of material into the lungs cannot be prevented, non-oral feeding may need to be implemented. This alternative, however, is both costly and unsatisfying to many individuals.

Therefore, strategies designed to improve swallowing safety and effectiveness in at-risk patients are commonly sought by clinicians working with dysphagic individuals. One well-known and frequently implemented technique involves the manipulation of bolus consistency. This is particularly considered when patients demonstrate difficulty with thin liquid bolus materials, e.g. water. Nutritional feeds are thickened to a safe and effective consistency based on results of clinical and instrumental assessments. In 2002, the American Dietetic Association established guidelines for thickened dietary supplements. Proposed in the Dysphagia Diet were viscosity ranges for thin (1-50 cP), nectar (51-350 cP)-like and honey-like (351-1750 cP) liquids.

Many of the currently available thickening products are based on starch, which does not dissolve well in some liquid products, tastes "starchy" and can form lumps over time. If patients find these products aversive, they are unlikely to consume them, thus precluding their potential value in optimizing swallow safety. In addition, if the stability of the consistency is in question, clinicians have difficulty recommending the product. Recently, gel thickeners have become available that are not associated with a bad taste, don't change the color of the liquid they're added to, and don't form lumps. In addition, they are purported to reach target viscosity rapidly, making them better suited to heated products, such as coffee or tea. The better texture and taste are due to the use of xanthan gum rather than starch. One such product is Resource® ThickenUp Clear. The gum-thickening agent was developed to improve solubility, viscosity and taste, as compared to currently available products.

However, although potential benefits of commercial gum-based products in altering bolus rheology are recognized, there have been few systematic efforts to alter bolus rheology in consideration of the type of aspiration relative to the swallowing reflex.

The inventors have found that treating dysphagic patients with standard boluses having increased viscosity such as nectar-like liquids may not only be ineffective with regard to improving swallowing function. For some patient groups, such standard bolus therapy is even likely to cause adverse effects and to increase aspiration prevalence. For example, thickened liquid boluses having a high shear viscosity were found to be beneficial in patients aspirating before and during swallowing. However, the same bolus was found to be detrimental for patients who tend to aspirate after the swallowing reflex.

Considering the prevalence of dysphagia, possible complications related thereto, and the costs associated with same, there is still a need for providing an improved method for treating swallowing disorders, which method can minimize the risk of standard bolus therapy and promotes safer swallowing of food boluses in patients suffering from aspiration. Such a method would improve the lives of a large and growing number of persons with swallowing impairments. Specific interventions (e.g., to promote oral health, help restore normal swallow, or reinforce a swallow-safe bolus) can enable persons to eat orally (vs. being tube fed and/or requiring PEG placement) and experience the psycho-social aspects of food associated with general well being while guarding against the potentially negative consequences that result from lack of adequate swallowing ability. Improvements in the intake of nutrition by dysphagic patients may also enable such patients to swallow a wider variety of food and beverage products safely and comfortably, which may lead to an overall healthier condition of the patient and prevent further health-related decline.

SUMMARY OF THE INVENTION

These needs are met by the present invention, which provides a novel and easy to implement method for treating a swallowing disorder in a patient suffering from aspiration, as well as a specific novel bolus for use in the treatment of a swallowing disorder in such patients.

Accordingly, in a first aspect, the invention relates to a method for treating a swallowing disorder in a patient suffering from aspiration, comprising the steps of: (1) Classifying the patient into a patient group selected from: (a) Aspiration before the swallowing reflex, (b) Aspiration during the swallowing reflex, (c) Aspiration after the swallowing reflex, (d) Aspiration before and during the swallowing reflex, (e) Aspiration before and after the swallowing reflex, or (f) Aspiration during and after the swallowing reflex; (2) Selecting a bolus having a cohesiveness specifically suited for the selected patient group according to step (1); (3) Administering the bolus to the patient.

A preferred embodiment of the present invention relates to the method according to the first aspect, wherein in step (2) the bolus is selected from cohesive thin liquids and cohesive thickened liquids.

In a further preferred embodiment of the first aspect of the invention, the bolus is selected from cohesive thin liquids having (i) a shear viscosity of less than about 50 mPas, preferably from 5 to 45 mPas, more preferably from 10 to 40 mPas, and most preferably from 20 to 30 mPas, when measured at a shear rate of 50 s−1, and (ii) a relaxation time, determined by a Capillary Breakup Extensional Rheometry (CaBER) experiment, of more than 10 ms (milliseconds) at a temperature of 20° C.

Preferably, in this embodiment of the first aspect of the invention the patient is classified into a patient group selected from: (a) Aspiration before the swallowing reflex, (c) Aspiration after the swallowing reflex, (d) Aspiration before and during the swallowing reflex, (e) Aspiration before and after the swallowing reflex, or (f) Aspiration during and after the swallowing reflex; and more preferably into a patient group selected from: (a) Aspiration before the swallowing reflex, (c) Aspiration after the swallowing reflex, or (e) Aspiration before and after the swallowing reflex.

In another preferred embodiment of the first aspect of the invention, the bolus is selected from cohesive thickened liquids having (i) a shear viscosity of more than about 50 mPas, preferably from 55 to 350 mPas, more preferably from 60 to 200 mPas, and most preferably from 70 to 100 mPas, when measured at a shear rate of 50 s−1, and (ii) a relaxation time, determined by a Capillary Breakup Extensional Rheometry (CaBER) experiment, of more than 10 ms (milliseconds) at a temperature of 20° C.

Preferably, in this embodiment of the first aspect of the invention the patient is classified into a patient group selected from: (c) Aspiration after the swallowing reflex, (d) Aspiration before and during the swallowing reflex, or (f) Aspiration during and after the swallowing reflex; and more preferably into a patient group selected from: (d) Aspiration before and during the swallowing reflex, or (f) Aspiration during and after the swallowing reflex.

It is further preferred that in the first aspect of the invention the bolus comprises at least one food grade biopolymer in a concentration of from at least 0.01 wt % to 25 wt %, preferably from at least 0.1 wt % to 15 wt %, and most preferably from at least 1 wt % to 10 wt %.

Preferably, the food grade biopolymer is selected from plant-extracted gums, plant-derived mucilages, or combinations thereof, wherein (a) the plant-extracted gums are selected from the group consisting of okra gum, konjac mannan, tara gum, locust bean gum, guar gum, fenugreek gum, tamarind gum, cassia gum, acacia gum, gum ghatti, pectins, cellulosics, tragacanth gum, karaya gum, or any combinations thereof, and preferably the plant-extracted gum is okra gum; (b) the plant-derived mucilages are selected from the group consisting of kiwi fruit mucilage, cactus mucilage, chia seed mucilage, psyllium mucilage, mallow mucilage, flax seed mucilage, marshmallow mucilage, ribwort mucilage, mullein mucilage, cetraria mucilage, or combinations thereof, and preferably the plant-derived mucilage is kiwi fruit mucilage and/or cactus mucilage.

In a further preferred embodiment of the method according to the first aspect of the invention, the bolus is in administrable form selected from the group consisting of a nutritional supplement, a full meal, a nutritionally complete formula, a pharmaceutical formulation, functional food, a beverage product, and combinations thereof.

In a second aspect, the invention relates to a bolus for use in the treatment of a swallowing disorder in a patient suffering from aspiration, wherein the patient suffers from one of the following: (a) Aspiration before the swallowing reflex, (b) Aspiration during the swallowing reflex, (c) Aspiration after the swallowing reflex, (d) Aspiration before and during the swallowing reflex, (e) Aspiration before and after the swallowing reflex, or (f) Aspiration during and after the swallowing reflex; wherein the bolus is selected from cohesive thin liquids and cohesive thickened liquids.

In a preferred embodiment of the second aspect of the invention, the bolus is selected from cohesive thin liquids having (i) a shear viscosity of less than about 50 mPas, preferably from 5 to 45 mPas, more preferably from 10 to 40 mPas, and most preferably from 20 to 30 mPas, when measured at a shear rate of 50 s−1, and (ii) a relaxation time, determined by a Capillary Breakup Extensional Rheometry (CaBER) experiment, of more than 10 ms (milliseconds) at a temperature of 20° C.

Preferably, in this embodiment the patient suffers from one of the following: (a) Aspiration before the swallowing reflex, (c) Aspiration after the swallowing reflex, (d) Aspiration before and during the swallowing reflex, (e) Aspiration before and after the swallowing reflex, or (f) Aspiration during and after the swallowing reflex; and even more preferably from: (a) Aspiration before the swallowing reflex, (c) Aspiration after the swallowing reflex, or (e) Aspiration before and after the swallowing reflex.

In another preferred embodiment of the second aspect of the invention the bolus is selected from cohesive thickened liquids having ((i) a shear viscosity of more than about 50 mPas, preferably from 55 to 350 mPas, more preferably from 60 to 200 mPas, and most preferably from 70 to 100 mPas, when measured at a shear rate of 50 s−1, and (ii) a relaxation time, determined by a Capillary Breakup Extensional Rheometry (CaBER) experiment, of more than 10 ms (milliseconds) at a temperature of 20° C.

Preferably, in this embodiment the patient suffers from one of the following: (c) Aspiration after the swallowing reflex, (d) Aspiration before and during the swallowing reflex, or (f) Aspiration during and after the swallowing reflex; and more preferably from: (d) Aspiration before and during the swallowing reflex, or (f) Aspiration during and after the swallowing reflex.

It is further preferred that in the second aspect of the invention, the bolus comprises at least one food grade biopolymer in a concentration of from at least 0.01 wt % to 25 wt %, preferably from at least 0.1 wt % to 15 wt %, and most preferably from at least 1 wt % to 10 wt %.

Preferably, said food grade biopolymer is selected from plant-extracted gums, plant-derived mucilages, or combinations thereof, wherein (a) the plant-extracted gums are selected from the group consisting of okra gum, konjac mannan, tara gum, locust bean gum, guar gum, fenugreek gum, tamarind gum, cassia gum, acacia gum, gum ghatti, pectins, cellulosics, tragacanth gum, karaya gum, or any combinations thereof, and preferably the plant-extracted gum is okra gum; (b) the plant-derived mucilages are selected from the group consisting of kiwi fruit mucilage, cactus mucilage, chia seed mucilage, psyllium mucilage, mallow mucilage, flax seed mucilage, marshmallow mucilage, ribwort mucilage, mullein mucilage, cetraria mucilage, or combinations thereof, and preferably the plant-derived mucilage is kiwi fruit mucilage and/or cactus mucilage.

In a further preferred embodiment of the second aspect of the invention, the bolus is in administrable form selected from the group consisting of a nutritional supplement, a full meal, a nutritionally complete formula, a pharmaceutical formulation, functional food, a beverage product, and combinations thereof.

Other aspects and embodiments of the present invention are described below.

DETAILED DESCRIPTION OF THE INVENTION

The present invention provides a method for treating a swallowing disorder in a patient suffering from aspiration, comprising the steps of: (1) Classifying the patient into a patient group selected from: (a) Aspiration before the swallowing reflex, (b) Aspiration during the swallowing reflex, (c) Aspiration after the swallowing reflex, (d) Aspiration before and during the swallowing reflex, (e) Aspiration before and after the swallowing reflex, or (f) Aspiration during and after the swallowing reflex; (2) Selecting a bolus having a cohesiveness specifically suited for the selected patient group according to step (1); (3) Administering the bolus to the patient.

Accordingly, the present invention further provides a bolus for use in the treatment of a swallowing disorder in a patient suffering from aspiration, wherein the patient suffers from one of the following: (a) Aspiration before the swallowing reflex, (b) Aspiration during the swallowing reflex, (c) Aspiration after the swallowing reflex, (d) Aspiration before and during the swallowing reflex, (e) Aspiration before and after the swallowing reflex, or (f) Aspiration during and after the swallowing reflex.

As used herein, term "bolus" refers to a physical portion of a food or beverage that can be swallowed by a human subject. Said bolus may be in solid, semi-solid or liquid form and may comprise one or more nutrients, foods or nutritional supplements. Preferably, the bolus is a liquid. It is further preferred that the bolus has a volume the patient can consume in one swallowing event. The preferred volume of the liquid bolus is from 1 to 50 ml, preferably from 5-20 ml, more preferably from 8-12 ml.

In the context of the present invention, the terms "treating", "treatment" and "to treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treating" and "to treat" are also intended to include the enhancement of one or more primary prophylactic or therapeutic measures. The terms "treatment," "treating" and "to treat" further intended to include the dietary management of a disease or condition or the dietary management for prophylaxis or prevention a disease or condition.

As used herein, the term "patient" is understood to include a mammal such as an animal and, more preferably, a human that is receiving or intended to receive treatment, as it is herein defined. While the terms "individual" and "patient" are often used herein to refer to a human, the invention is not so limited. Accordingly, the terms "individual" and "patient" refer to any animal, mammal or human having or at risk for a medical condition that can benefit from the treatment.

In this context, "mammal" includes, but is not limited to, rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

In the context of the present invention, the term "swallowing disorder" refers to any kind of physiologic dysfunction and/or disorder that is associated with difficulties and/or an impairment of swallowing, and to the symptoms thereof, which in medical terms is referred to as dysphagia, including esophageal and oral pharyngeal dysphagia, and aspiration.

Esophageal dysphagia affects a large number of individuals of all ages, but is generally treatable with medications and is considered a less serious form of dysphagia. Esophageal dysphagia is often a consequence of mucosal, mediastinal, or neuromuscular diseases. Mucosal (intrinsic) diseases narrow the lumen through inflammation, fibrosis, or neoplasia associated with various conditions (e.g., peptic stricture secondary to gastroesophageal reflux disease, esophageal rings and webs [e.g., sideropenic dysphagia or Plummer-Vinson syndrome], esophageal tumors, chemical injury [e.g., caustic ingestion, pill esophagitis, sclerotherapy for varices], radiation injury, infectious esophagitis, and eosinophilic esophagitis). Mediastinal (extrinsic) diseases obstruct the esophagus by direct invasion or through lymph node enlargement associated with various conditions (tumors [e.g., lung cancer, lymphoma], infections [e.g., tuberculosis, histoplasmosis], and cardiovascular [dilated auricula and vascular compression]). Neuromuscular diseases may affect the esophageal smooth muscle and its innervation, disrupting peristalsis or lower esophageal sphincter relaxation, or both, commonly associated with various conditions (achalasia [both idiopathic and associated with Chagas disease], scleroderma, other motility disorders, and a consequence of surgery [i.e., after fundoplication and anti-reflux interventions]). It is also common for individuals with intraluminal foreign bodies to experience acute esophageal dysphagia.

Oral pharyngeal dysphagia, on the other hand, is a very serious condition and is generally not treatable with medication. Oral pharyngeal dysphagia also affects individuals of all ages, but is more prevalent in older individuals. Worldwide, oral pharyngeal dysphagia affects approximately 22 million people over the age of 50. Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervation of the swallow reflex. It is also common for individuals with progressive neuromuscular diseases, such as Parkinson's Disease, to experience increasing difficulty in swallowing initiation. Representative causes of oropharyngeal dysphagia include those associated neurological illnesses (brainstem tumors, head trauma, stroke, cerebral palsy, Guillain-Barre syndrome, Huntington's disease, multiple sclerosis, polio, post-polio syndrome, Tardive dyskinesia, metabolic encephalopathies, amyotrophic lateral sclerosis, Parkinson's disease, dementia), infectious illnesses (diphtheria, botulism, Lyme disease, syphilis, mucositis [herpetic, cytomegalovirus, candida, etc.]), autoimmune illnesses (lupus, scleroderma, Sjogren's syndrome), metabolic illnesses (amyloidosis, cushing's syndrome, thyrotoxicosis, Wilson's disease), myopathic illnesses (connective tissue disease, dermatomyositis, myasthenia gravis, myotonic dystrophy, oculopharyngeal dystrophy, polymyositis, sarcoidosis, paraneoplastic syndromes, inflammatory myopathy), iatrogenic illnesses (medication side effects [e.g., chemotherapy, neuroleptics, etc.], post surgical muscular or neurogenic, radiation therapy, corrosive [pill injury, intentional]), and structural illnesses (cricopharyngeal bar, Zenker's diverticulum, cervical webs, oropharyngeal tumors, osteophytes and skeletal abnormalities, congenital [cleft palate, diverticulae, pouches, etc.]).

Severity of dysphagia may vary from: (i) minimal (perceived) difficulty in safely swallowing foods and liquids, (ii) an inability to swallow without significant risk for aspiration or choking, and (iii) a complete inability to swallow. Commonly, the inability to properly swallow foods and liquids may be due to food boluses being broken up into smaller fragments, which may enter the airway or leave unwanted residues in the oropharyngeal and/or esophageal tract during the swallowing process, which symptom is clinically referred to as "aspiration". If enough material enters the lungs through aspiration, it is possible that the patient may drown on the food/liquid that has built up in the lungs. Even small volumes of aspirated food may lead to bronchopneumonia infection, and chronic aspiration may lead to bronchiectasis and may cause some cases of asthma.

It has been surprisingly found that certain patient populations are more likely to aspirate at one time or another relative to the swallowing reflex. For example, if a patient has reduced sensation, aspiration is particularly likely to occur before the swallowing reflex. Patients with very poor pharyngeal constriction may be more likely to aspirate after the swallowing reflex, on material remaining post-swallow in an uncleared pharynx. If complete airway closure is not possible, aspiration during the swallowing reflex, i.e. during the time of maximum (but incomplete) airway closure may be likely. Aspiration "before", "during" and "after" the swallowing reflex do not mutually exclude each other, i.e. subjects may exhibit more than one type of aspiration such as aspiration before and during the swallowing reflex, aspiration before and after the swallowing reflex, or aspiration during and after the swallowing reflex.

According to these findings, the method of the invention comprises in a first step classifying the patient into a specific patient group selected from (a) Aspiration before the swallowing reflex, (b) Aspiration during the swallowing reflex, (c) Aspiration after the swallowing reflex, (d) Aspiration before and during the swallowing reflex, (e) Aspiration before and after the swallowing reflex, or (f) Aspiration during and after the swallowing reflex. An implication of this classification is that a particular bolus type may be better suited to a particular patient group, depending on when aspiration occurs, or is most likely to occur.

Classifying the patients into one of these groups may be accomplished by any method known in the art. In the studies underlying the present invention, a standard videofluoroscopy technique was used (as described e.g. in Kendall and Leonard, "Dysphagia", 2000) to determine whether aspiration in a patient occurs before, during or after, before and during, before and after, or during and after the swallowing reflex.

Bolus

Therefore, the method of the invention comprises selecting and administering to a patient a bolus which is specifically suited for the type of aspiration occurring in the patient, wherein the bolus is not only modified with regard to its shear viscosity, but with regard to at least one further rheological property such as its cohesiveness.

Preferably, said bolus is selected from cohesive thin liquids and cohesive thickened liquids.

Cohesive Thin Liquids

It was surprisingly found that in patients who aspirate (a) before the swallowing reflex, (c) after the swallowing reflex, (d) before and during the swallowing reflex, (e) aspiration before and after the swallowing reflex, or (f) during and after the swallowing reflex, aspiration prevalence could be significantly reduced by administering a bolus having the rheological properties of a cohesive thin liquid.

In one preferred embodiment, that cohesive thin liquid bolus has (i) a shear viscosity of less than about 50 mPas, preferably from 5 to 45 mPas, more preferably from 10 to 40 mPas, and most preferably from 20 to 30 mPas, when measured at a shear rate of 50 s−1, and (ii) a relaxation time, determined by a Capillary Breakup Extensional Rheometry (CaBER) experiment, of more than 10 ms (milliseconds) at a temperature of 20° C.

Shear viscosity is a commonly measured rheological property, which is often referred to as simply viscosity, and which may be determined by any method known in the art. In the present invention, shear viscosity was determined using concentric cylinders in a standard research-grade rheometer (Anton Paar MCR). Said parameter describes the reaction of a material to applied shear stress. In other words, shear viscosity is the ratio between "stress" (force per unit area) exerted on the surface of a fluid, in the lateral or horizontal direction, to the change in velocity of the fluid as you move down in the fluid (a "velocity gradient").

Cohesiveness is a parameter that relates to the ability of a portion of liquid to hold together when being stretched (extended, elongated) in a flow, e.g. passing through a constriction, dewetting of a drop on a surface or thinning of a liquid filament.

In the context of the present disclosure, the relaxation time of a bolus as a measure of its cohesiveness was determined by a Capillary Breakup Extensional Rheometry (CaBER) experiment. The herein used Capillary Breakup Extensional Rheometer is an example for a rheometer applying extensional stress. During the CaBER experiment as performed herein for measuring the relaxation time of the bolus, a drop of said bolus is placed between two vertically aligned and parallel circular metal surfaces, both having a diameter of 6 mm. The metal surfaces are then rapidly separated linearly over a time interval of 50 ms (milliseconds). The filament formed by this stretching action subsequently thins under the action of interfacial tension and the thinning process is followed quantitatively using a laser sheet measuring the filament diameter at its mid-point. The relaxation time in a CaBER experiment is determined by plotting the normalised natural logarithm of the filament diameter during the thinning process versus time and determining the slope of the linear portion (dln (D/D0)/dt) of this curve, where D is the filament diameter, D0 the filament diameter at time zero and t the time of filament thinning. The relaxation time in this context is then defined as minus one third (−⅓) times the inverse of this slope, i.e. −1/(3dln(D/D0)/dt).]

Administering a bolus of the cohesive thin liquid type was found to be particularly beneficial in patients who were classified into one of the groups of (a) Aspiration before the swallowing reflex, (c) Aspiration after the swallowing reflex, or (e) Aspiration before and after the swallowing reflex.

Cohesive Thickened Liquids

It was further found that in patients who aspirate (c) after the swallowing reflex, (d) before and during the swallowing reflex, or (f) during and after the swallowing reflex, aspiration prevalence could be significantly reduced by administering a bolus having the rheological properties of a cohesive thickened liquid.

It is preferred that said cohesive thickened liquid bolus has (i) a shear viscosity of more than about 50 mPas, preferably from 55 to 350 mPas, more preferably from 60 to 200 mPas, and most preferably from 70 to 100 mPas, when measured at a shear rate of 50 s−1, and (ii) a relaxation time, determined by a Capillary Breakup Extensional Rheometry (CaBER) experiment, of more than 10 ms (milliseconds) at a temperature of 20° C., wherein said shear viscosity and relaxation time are determined as set out above for cohesive thin liquids.

Administering a bolus of the cohesive thickened liquid type was found to be particularly beneficial in patients who were classified into one of the groups of (d) Aspiration before and during the swallowing reflex, or (f) Aspiration during and after the swallowing reflex.

Biopolymers

In an embodiment, the bolus comprises at least one food grade biopolymer, preferably in a concentration of from at least 0.01 wt % to 25 wt %, preferably from at least 0.1 wt % to 15 wt %, and most preferably from at least 1 wt % to 10 wt %.

Said food grade biopolymer may preferably be selected from the group consisting of botanical hydrocolloids, microbial hydrocolloids, animal hydrocolloids, algae hydrocolloids and any combination thereof.

Suitable algae hydrocolloids preferably include agar, carrageenan, alginate or combinations thereof. The microbial hydrocolloids may be selected from xanthan gum, gellan gum, curdlan gum, or combinations thereof.

Botanical hydrocolloids that may be used in the present invention are preferably selected from plant-extracted gums, plant-derived mucilages, and combinations thereof.

As used herein, plant-extracted gums preferably include any one of okra gum, glucomannans (konjac mannan), galactomannans (tara gum, locust bean gum, guar gum, fenugreek gum), tamarind gum, cassia gum, gum Arabic (acacia gum), gum ghatti, pectins, cellulosics, tragacanth gum, karaya gum, and combinations thereof. Okra gum is particularly preferred.

As used herein, plant-derived mucilages are preferably selected from the group consisting of kiwi fruit mucilage, cactus mucilage, chia seed mucilage, psyllium mucilage, mallow mucilage, flax seed mucilage, marshmallow mucilage, ribwort mucilage, mullein mucilage, cetraria mucilage, and combinations thereof. In a particularly preferred embodiment, the plant-derived mucilage is kiwi fruit mucilage and/or cactus mucilage.

In another preferred embodiment, the plant-derived mucilage is kiwi fruit mucilage. In the context of this disclosure, kiwi fruit mucilage is preferably derived from the stem pith of kiwi fruit, which contains about 20% of mucilage and typically represents the plant waste material remaining from kiwi fruit agriculture.

In the context of this disclosure, the gums and mucilages are preferably food grade and can be commercially obtained from numerous suppliers.

Alternatively, the above gums and mucilages may be obtained by any suitable extraction method known in the art. For example, gums and mucilages may be extracted by a method comprising the steps of soaking the raw plant material with 10 times of its weight of distilled water and keeping it overnight. A viscous solution is obtained, which is passed through a muslin cloth. The gum or mucilage is precipitated by addition of 95% by weight of ethanol in a ratio of about 1:1 by continuous stirring. A coagulated mass is obtained, which is subsequently dried in an oven at 40 to 45° C., powdered by passing through a sieve and stored in an airtight container.

In the context of this disclosure it is particularly preferred that the at least one bolus comprises a food grade biopolymer selected from okra gum, cactus mucilage and kiwi fruit mucilage, or any combination thereof.

In an embodiment, the bolus comprises at least one food grade biopolymer selected from okra gum, cactus mucilage, kiwi fruit mucilage, and combinations thereof and a further food-grade biopolymer selected from starch, modified starch, xanthan gum, guar gum, carageenan, tara gum, locust been gum, alginates and pectins.

In yet another embodiment, the bolus is in administrable form selected from the group consisting of a nutritional supplement, a full meal, a nutritionally complete formula, a pharmaceutical formulation, functional food, a beverage product, and combinations thereof.

A kit comprising one or more containers comprising cohesive thin liquids and cohesive thickened liquids each container comprising a cohesive thin liquid or a cohesive thickened liquid respectively is also encompassed by the scope of the invention. The cohesive thin liquids and cohesive thickened liquids can be as defined above.

Further Ingredients

In a further embodiment, the bolus of the invention comprises a suspension of rigid particles in a cohesive liquid, preferably wherein the rigid particles have a size of from 100 nm to 1 mm, preferably from 200 nm to 900 nm, from 300 nm to 800 nm, from 400 nm to 700 nm, or from 500 nm to 600 nm. It is also preferred that those rigid particles are comprised in the bolus in an amount of from 1 to 50% by volume, preferably in an amount of from 5 to 40% by volume, 10 to 30% by volume, or 15 to 20% by volume. The rigid particles may be comprised of any food grade material, and are preferably selected from cocoa, coffee or mustard particles.

The bolus may further comprise a high molecular weight protein, which is preferably selected from collagen-derived proteins such as gelatin, plant proteins such as potato, pea, lupin, etc., or other proteins of sufficiently high molecular weight (MW=100 kDa and above).

The bolus may further comprise a source of dietary protein including, but not limited to animal protein (such as meat protein or egg protein), dairy protein (such as casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate)), vegetable protein (such as soy protein, wheat protein, rice protein, and pea protein), or combinations thereof. In an embodiment, the protein source is selected from the group consisting of whey, chicken, corn, caseinate, wheat, flax, soy, carob, pea, or combinations thereof.

The bolus may further comprise a source of carbohydrates. Any suitable carbohydrate may be used in the bolus of the invention including, but not limited to, sucrose, lactose, glucose, fructose, corn syrup solids, maltodextrin, modified starch, amylose starch, tapioca starch, corn starch or combinations thereof.

The bolus may further comprise a source of fat. The source of fat may include any suitable fat or fat mixture. For example, the fat source may include, but is not limited to, vegetable fat (such as olive oil, corn oil, sunflower oil, rapeseed oil, hazelnut oil, soy oil, palm oil, coconut oil, canola oil, lecithins, and the like), animal fats (such as milk fat) or combinations thereof.

The bolus may further comprise one or more prebiotics. As used herein, a "prebiotic" is a food substance that selectively promotes the growth of beneficial bacteria or inhibits the growth or mucosal adhesion of pathogenic bacteria in the intestines. They are not inactivated in the stomach and/or upper intestine or absorbed in the gastrointestinal tract of the person ingesting them, but they are fermented by the gastrointestinal microflora and/or by probiotics. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, leman, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

The bolus may further comprise one or more probiotics. As used herein, probiotic micro-organisms (hereinafter "probiotics") are food-grade microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. In general, it is believed that these micro-organisms inhibit or influence the growth and/or metabolism of pathogenic bacteria in the intestinal tract. The probiotics may also activate the immune function of the host. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

The bolus may further comprise one or more amino acids. Non-limiting examples of suitable amino acids include alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

The bolus may further comprise one or more synbiotics, sources of ω-3 fatty acids, and/or phytonutrients. As used herein, a synbiotic is a supplement that contains both a prebiotic and a probiotic as defined above that work together to improve the microflora of the intestine. Non-limiting examples of sources of ω-3 fatty acids such α-linolenic acid ("ALA"), docosahexaenoic acid ("DHA") and eicosapentaenoic acid ("EPA") include fish oil, krill, poultry, eggs, or other plant or nut sources such as flax seed, walnuts, almonds, algae, modified plants, etc. Non-limiting examples of phytonutrients include quercetin, curcumin and limonin and combinations thereof.

The bolus may further comprise one or more antioxidants. As used herein, the term "antioxidant" is understood to include any one or more of various substances such as beta-carotene (a vitamin A precursor), vitamin C, vitamin E, and selenium that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin B1, vitamin B6, vitamin B12, vitamin C, vitamin D, vitamin E, zeaxanthin, or combinations thereof.

The bolus may further comprise fiber or a blend of different types of fiber. The fiber blend may contain a mixture of soluble and insoluble fibers. Soluble fibers may include, for example, fructooligosaccharides, acacia gum, inulin, etc. Insoluble fibers may include, for example, pea outer fiber.

The bolus may further comprise other functional ingredients including chitosans and protein aggregates. Chitosans are linear polysaccharides composed of randomly distributed β-(1-4)-linked D-glucosamine (deacetylated unit) and N-acetyl-D-glucosame (acetylated unit). Among other potential benefits, chitosans have natural antibacterial properties, aid in drug delivery, and are known to rapidly clot blood. Protein aggregates are coalescences of miss-folded proteins driven by interactions between solvent-exposed hydrophobic surfaces that are normally buried within a protein's interior.

The terms "protein," "peptide," "oligopeptides" or "polypeptide," as used herein, are understood to refer to any composition that includes, a single amino acids (monomers), two or more amino acids joined together by a peptide bond (dipeptide, tripeptide, or polypeptide), collagen, precursor, homolog, analog, mimetic, salt, prodrug, metabolite, or fragment thereof or combinations thereof. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention include, but are not limited to, acetylation, acylation, ADP-ribosylation, amidation, covalent attachment of a flavanoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol ("GPI") membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non-linear polypeptides, consisting of alternating repeats of a peptide.

The following examples are provided to further illustrate the present invention. They are not intended to be limiting the scope of the present invention.

EXAMPLES

Example 1

Study outline for determining the aspiration type

The ability of the claimed method to specifically address different specific types of dysphagic conditions can be validated clinically through an interventional crossover study. In such a study, three different liquid bolus types selected from conventional thickened liquids, cohesive thin liquids and cohesive thin liquids are administered to patients diagnosed for oropharyngeal dysphagia. A standard videofluoroscopy method is used for determining the aspiration type. Aspiration of a liquid bolus before, during or after an active swallowing reflex can be differentiated by using this technique and thus allows to unambiguously validate the ability of a given bolus to ameliorate specific types of aspirations as well as combinations thereof.

Results

|  | Thickened liquids | Cohesive thin liquids | Cohesive thickened liquids |
|---|---|---|---|
| Aspiration before swallowing reflex | Currently best solution - improves control and accidental transfer into pharynx | Better solution than thickened liquids: more natural in appearance and still preventing accidental transfer because of high force need to propel, open siphon effect | Added value compared to cohesive thin liquids in some cases |
| Aspiration during swallowing reflex | The only solution to allow more adaptation time for the airway protection reflex | Not beneficial | No added value compared to ordinary thickened liquids, but equally good |
| Aspiration after swallowing reflex | Not helpful, can be detrimental (residues) | Beneficial due to better cohesiveness in dewetting of drops. | Better than ordinary thickened liquids, but worse than cohesive thin ones. |
| Before AND during | Good solution. | Better solution than thickened liquids, depends on seriousness of «during» (coordination) problem | The best solution |
| Before AND after | Not helpful if the «after» (residue) problem is severe | The best solution. | No added benefit compared to cohesive thin liquids |
| During AND after | Not helpful if the «after» (residue) problem is severe | Better solution than thickened liquids, depends on seriousness of «during» (coordination) problem | The best solution. |
| All three | Needs careful diagnosis and individually tailored recommendations | | |

Discussion

Aspiration before the swallowing is expected in roughly half of all patients exhibiting aspiration. In these patients, cohesive thin liquids were shown to have the best effect in ameliorating aspiration prevalence.

Aspiration during the swallowing reflex is expected in roughly one third of all patients exhibiting aspiration. In these patients, conventional thickened liquids and cohesive thickened liquids were shown to have equally good effects in ameliorating aspiration prevalence.

Aspiration after the swallowing reflex is expected in roughly half of all patients exhibiting aspiration. In these patients, cohesive thin liquids were shown to have the best effect in ameliorating aspiration prevalence, followed by cohesive thickened liquids. Conventional thickened liquids proved to be detrimental in these patients.

A combination of aspiration before and during the swallowing reflex is expected in less than one tenth of all patients exhibiting aspiration. In these patients, cohesive thickened liquids proved to be the best solution, followed by cohesive thin liquids, which were shown to have an improved effect in ameliorating aspiration prevalence when compared to conventional thickened liquids.

A combination of aspiration before and after the swallowing reflex is expected in less than one tenth of all patients exhibiting aspiration. In these patients, cohesive thin liquids were shown to have the best effect in ameliorating aspiration prevalence. Conventional thickened liquids proved to be rather detrimental in these patients.

A combination of aspiration during and after the swallowing reflex is expected in less than one tenth of all patients exhibiting aspiration. In these patients, cohesive thickened liquids were shown to be the best solution, followed by cohesive thin liquids. Conventional thickened liquids proved to be rather detrimental in these patients.

The invention claimed is:

1. A method for mitigating difficulty in and/or impairment of swallowing in a patient suffering from aspiration, the method comprising:
   (1) Classifying the patient into a patient group selected from the group consisting of:
      (a) Aspiration before the swallowing reflex,
      (b) Aspiration during the swallowing reflex,
      (c) Aspiration after the swallowing reflex,
      (d) Aspiration before and during the swallowing reflex,
      (e) Aspiration before and after the swallowing reflex, and
      (f) Aspiration during and after the swallowing reflex;
   (2) Supplying (i) a first liquid having a shear viscosity from 5 to 45 mPas when measured at a shear rate of 50 s−1 and a relaxation time, determined by a Capillary Breakup Extensional Rheometry (CaBER) experiment, of more than 10 ms (milliseconds) at a temperature of 20° C. and (ii) a second liquid having a shear viscosity more than 50 mPas when measured at a shear rate of 50 s−1 and a relaxation time, determined by a CaBER experiment, of more than 10 ms (milliseconds) at a temperature of 20° C.;
   (3) Selecting a bolus based on the selected patient group according to step (1) from the first liquid and the second liquid; and
   (4) Administering the bolus to the patient, wherein the bolus comprises at least one food grade biopolymer selected from the group consisting of okra gum, kiwi fruit mucilage, cactus mucilage, and combinations thereof.

2. The method according to claim 1, wherein the bolus comprises the at least one food grade biopolymer in a concentration from at least 0.01 wt % to 25 wt %.

3. The method according to claim 1, wherein the bolus is in an administrable form selected from the group consisting of a nutritional supplement, a full meal, a nutritionally complete formula, a pharmaceutical formulation, functional food, a beverage product, and combinations thereof.

4. The method according to claim 1, wherein the second liquid has a shear viscosity from 55 to 350 mPas when measured at a shear rate of 50 s−1.

5. The method according to claim 1 wherein the bolus comprises the at least one food grade biopolymer in a concentration from 1 wt % to 10 wt %.

6. The method according to claim 1, wherein the patient is classified into one of the patient groups (a), (c), (d), (e) and (f); and the bolus administered to the patient is the first liquid.

7. The method according to claim 1, wherein the patient is classified into one of the patient groups (c), (d) and (f); and the bolus administered to the patient is the second liquid.

* * * * *